United States Patent [19]

Stevenson

[11] Patent Number: 4,687,013

[45] Date of Patent: Aug. 18, 1987

[54] FLUERIC PARTIAL PRESSURE SENSOR

[75] Inventor: George F. Stevenson, Yeovil, England

[73] Assignee: Normalair-Garrett (Holdings) Limited, Yeovil, England

[21] Appl. No.: 828,659

[22] Filed: Feb. 12, 1986

[30] Foreign Application Priority Data

Feb. 22, 1985 [GB] United Kingdom ............... 8504567

[51] Int. Cl.⁴ .................. G01N 7/00; F16K 17/36
[52] U.S. Cl. ................................. 137/7; 137/81.1; 137/805; 128/204.24; 128/204.29; 73/23; 55/163
[58] Field of Search .......... 73/23; 128/204.24, 204.29; 137/81.1, 7, 805; 55/163

[56] References Cited

U.S. PATENT DOCUMENTS 4,407,153  10/1983  Furlong et al. ............... 137/804
4,501,293  2/1985   Furlong et al. ............... 137/804

Primary Examiner—A. Michael Chambers
Attorney, Agent, or Firm—Larson and Taylor

[57] ABSTRACT

A flueric partial pressure sensor (10) includes a flueric bridge sensor (10a) having two bridge legs (11, 12) adapted for sensing a reference-gas and a sample-gas. A linear resistor (14, 15) and an orifice resistor (16, 17) are incorporated in each leg and arranged to cause asymmetric flow rates therethrough. Inlets to the two bridge legs are subject to a datum pressure within a datum pressure chamber (38) so that a change of datum pressure automatically changes control signals output by the sensor. The partial pressure sensor is disclosed in combination with a molecular sieve type gas concentration system (24) in an on-board oxygen enrichment of air system for an aircraft and enables the oxygen concentration in oxygen enriched air delivered by the system to be appropriate to breathing requirement at an altitude intermediate aircraft cabin and ambient atmospheric pressures.

8 Claims, 2 Drawing Figures

FLUERIC PARTIAL PRESSURE SENSOR

BACKGROUND OF THE INVENTION

1. Field of the Invention

This invention relates to flueric partial pressure sensors and is more particularly concerned with a flueric partial pressure sensor for use in controlling a molecular sieve type gas separation system in an on-board oxygen enrichment of air system for an aircraft.

2. Description of the Prior Art

U.S. Pat. No. 4,407,153 which corresponds to EP-A-0 036 285 (Normalair-Garrett) discloses a flueric partial pressure sensor which may be incorporated in a molecular sieve type gas separation system (MSOGS) for delivering oxygen-enriched air to aircrew members, an example of such a system being disclosed in and EP-A-0 129 304 (Normalair-Garrett) which corresponds to pending U.S. patent application Ser. No. 595,303 filed 30 Mar., 1984.

In aircraft capable of long range flight at altitudes up to, say, 60,000 feet (18,290 meters), it is desirable and practicable, for the comfort and efficiency of the crew, to so pressurise the aircraft cabin that the cabin pressure does not fall below an altitude equivalent of, say, 8,000 feet (2,440 meters) up to a chosen aircraft altitude - say 45,000 feet (13,720 meters) - and thereafter to maintain the same cabin to atmosphere pressure difference with increasing aircraft altitude.

Whilst failure of cabin pressurisation equipment is a remote possibility provision must be made for possible depressurisation which, at worst, could be instant. In anticipation of instant depressurisation it is expedient, medically, to increase the oxygen concentration in the air breathed by the crew when the aircraft is above a certain altitude. Thus, whilst the cabin pressure may be held at an 8,000 feet (2,440 meters) equivalent up to the chosen altitude of, say, 45,000 feet (13,720 meters), the oxygen concentration in the air delivered from the breathing system should be made to increase beyond the 8,000 feet (2,440 meters) equivalent concentration value - about 29% - as the aircraft climbs above an aircraft altitude of, approximately, 30,000 feet (9,145 meters).

Furthermore, a flueric partial pressure sensor as disclosed in U.S. Pat. No. 4,407,153 will operate only at absolute pressures up to an altitude equivalent of about 25,000 feet (7,620 meters), pressure above this altitude being insufficient to drive the sensor.

SUMMARY OF THE INVENTION

It is an object of the present invention to provide a method of changing control signals output by a flueric partial pressure sensor at a predetermined pressure condition.

It is another object of the present invention to provide a method of controlling a molecular sieve type gas separation system forming part of an on-board oxygen enrichment of air system for an aircraft to automatically increase the oxygen concentration of oxygen enriched air output by the system above a predetermined altitude.

A further object of the invention is the provision of a flueric partial pressure sensor for use in controlling a molecular sieve type gas separation system delivering oxygen-enriched air in an on-board oxygen enrichment of air system for an aircraft so as to automatically increase the concentration of oxygen in the oxygen-enriched air above a predetermined altitude.

Accordingly, one aspect of the invention provides a method of changing control signals output by a flueric partial pressure sensor, said sensor comprising a flueric bridge having two legs adapted for respectively sensing a reference-gas and a sample-gas mixture, each leg including a linear flow resistor and an orifice flow resistor having values arranged to cause asymmetric flow rates through the two legs so that at a particular partial pressure of a constituent gas in the sample-gas mixture the bridge is in balance, the method including the steps of pressure referencing the reference-gas and the sample-gas mixture to a datum pressure and changing the datum pressure to change the control signals output by the sensor.

In a further aspect, the invention provides a method of controlling an on-board oxygen enrichment of air system for an aircraft to automatically increase the oxygen concentration of oxygen-enriched air output by the system above a predetermined altitude, the system comprising a molecular sieve type gas separation system (MSOGS) arranged to deliver oxygen-enriched air to an outlet by adsorbing nitrogen from supply air fed to the MSOGS, and a flueric partial pressure sensor arranged to compare a reference bleed of supply air to the MSOGS with a sample bleed of oxygen-enriched air delivered by the MSOGS and to output signals for the control of the MSOGS, the method including the steps of referencing the reference bleed of supply air and the sample bleed of oxygen-enriched air to a datum pressure, and changing the datum pressure above a predetermined aircraft altitude to a pressure value intermediate the pressure within a cabin to which the oxygen-enriched air is supplied and the atmospheric pressure ambient to the aircraft whereby with change in aircraft altitude above the predetermined altitude the signals output by the sensor for control of the MSOGS are automatically varied to increase the oxygen concentration of the oxygen-enriched air.

In another aspect, the invention provides a flueric partial pressure sensor including a flueric bridge having two legs, one of said legs sensing a reference-gas and the other of said legs sensing a sample-gas mixture, a linear flow resistor and an orifice flow resistor arranged in series in each of said legs, a pressure sensing port in each leg positioned between the linear flow resistor and the orifice flow resistor, a datum pressure chamber, a reference-gas supply line and a sample-gas mixture supply line to said bridge legs passing through said datum pressure chamber, means in said supply lines for pressure referencing the reference-gas and the sample-gas mixture to datum pressure in said datum pressure chamber, means in said datum pressure chamber providing a restricted flow communication with a first pressure region, pressure responsive means in said datum pressure chamber for providing communication with a second pressure region of different pressure from said first pressure region, the values of said linear flow resistors and orifice flow resistors being arranged to cause asymmetric flow rates through the two said legs so that the pressure sensing ports are in-balance at a predetermined partial pressure of a constituent gas in the sample-gas mixture whereby a change in datum pressure automatically changes control signals output by the sensor.

In yet another aspect, the invention provides an on-board oxygen enrichment of air system for an aircraft, including a molecular sieve type gas separation system (MSOGS) arranged to deliver oxygen-enriched air to an outlet by adsorbing nitrogen from supply air fed to the system and a flueric partial pressure sensor, said partial pressure sensor comprising a flueric bridge having two bridge legs, one of said bridge legs being arranged for sensing a reference bleed of supply air to the MSOGS and the other said bridge leg being arranged for sensing a sample bleed of oxygen-enriched air delivered by the MSOGS, a linear flow resistor and an orifice flow resistor arranged in series in each of said legs, a pressure sensing port in each leg positioned between the linear flow resistor and the orifice flow resistor, a datum pressure chamber, lines carrying the reference bleed of supply air and the sample bleed of oxygen-enriched air to said bridge legs passing through said datum pressure chamber, means in said supply lines for pressure referencing the reference bleed of supply air and the sample bleed of oxygen-enriched air to datum pressure in said datum pressure chamber, means in said datum pressure chamber providing a restricted flow communication with pressure in a cabin to which the oxygen-enriched air is supplied by the MSOGS, means in said datum pressure chamber for providing above a predetermined aircraft altitude a datum pressure value intermediate the pressure within the cabin and atmospheric pressure ambient to the aircraft, the values of said linear flow resistors and orifice flow resistors being arranged to cause asymmetric flow rates through the two said bridge legs so that the pressure sensing ports are in-balance at a predetermined partial pressure of oxygen in the sample bleed of oxygen-enriched air whereby with change in aircraft altitude above the predetermined altitude the signals output by the sensor for control of the MSOGS are automatically varied to increase the oxygen concentration of the oxygen-enriched air.

The means in said datum pressure chamber for providing a datum pressure value intermediate cabin pressure and aircraft ambient atmospheric pressure preferably comprises a pressure responsive valve arranged to open the datum pressure chamber to aircraft ambient atmosphere.

The means in the supply lines for pressure referencing the reference bleed of supply air and the sample bleed of oxygen-enriched air to datum pressure may comprise shrouds which are open to the datum pressure chamber.

Preferably, the partial pressure sensor is wholly located within the datum pressure chamber.

BRIEF DESCRIPTION OF THE DRAWING

An exemplary embodiment of the invention will now be described with reference to the accompanying drawing in which.

DETAILED DESCRIPTION OF THE INVENTION

The exemplary embodiment now described is suitable for aircraft use in the obtainment of medically desirable oxygen concentration in oxygen-enriched air in a pressurised cabin of an aircraft which may fly at altitudes up to 60,000 feet (18,290 meters). As discussed above it is desirable for the oxygen concentration of the air delivered for breathing by aircrew in such a cabin to be increased above that normal to the pertaining cabin pressure when the altitude of the aircraft is above approximately 30,000 feet (9,145 meters). Apparatus for achieving this desirable breathing air condition includes a flueric partial pressure sensor in accordance with the present invention operated in combination with a molecular sieve type gas separation system (MSOGS) arranged to reduce the nitrogen content of raw air supplied to the system from a compressor stage of an aircraft engine before delivering to the aircrew breathing system.

Figure 1:
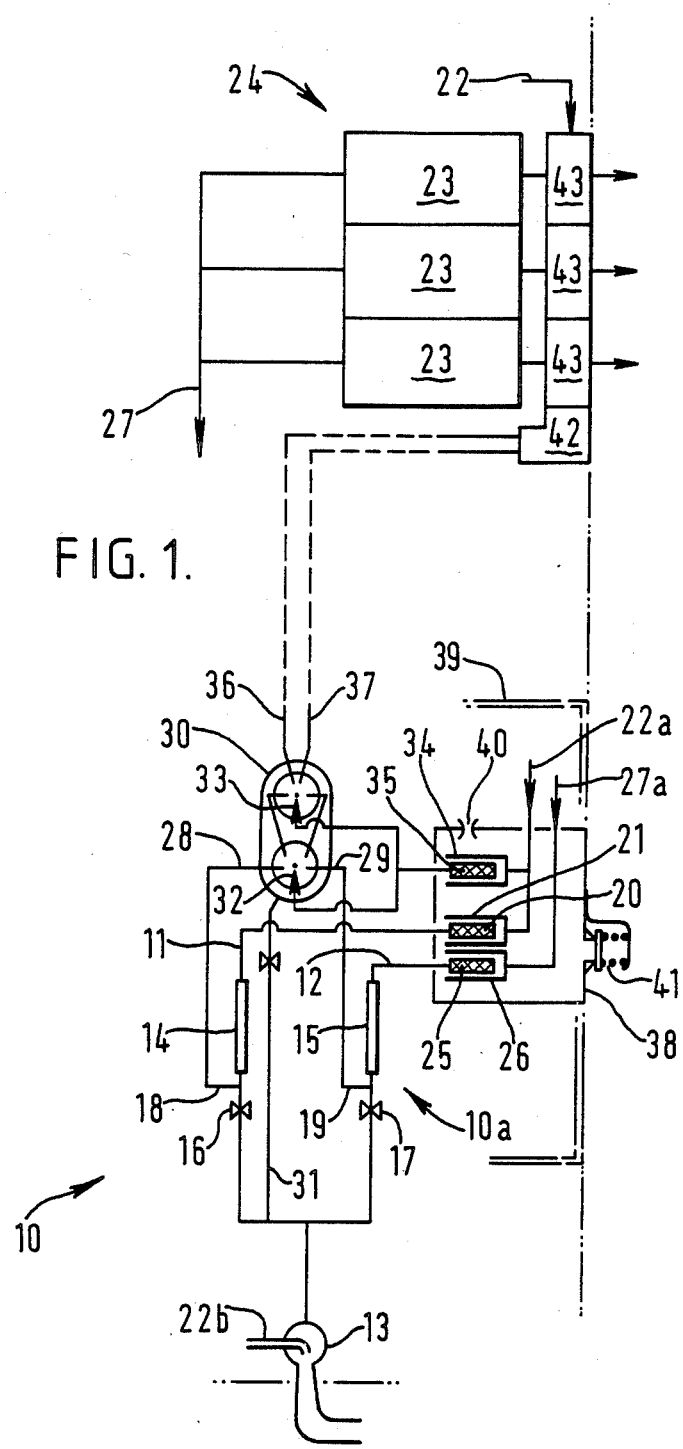
FIG. 1 schematically illustrates an embodiment of a flueric partial pressure sensor in an aircraft application.

A flueric partial pressure sensor 10 (FIG. 1) comprises a bridge sensor 10a having a reference-gas leg 11 and a sample-gas leg 12 conjoined at their downstream ends to provide a single outlet by way of a flueric aspirator 13. The legs 11, 12 include linear resistors 14, 15, respectively, positioned upstream of respective orifice resistors 16, 17, bridge pressure sensing ports 18, 19 being positioned intermediate the linear and orifice resistors in the respective legs. The reference-gas leg 11 is provided at its entrance with a filter 20 which is retained in a freely venting shroud 21 that receives by way of a duct 22a a bleed of raw air taken from a line 22 which supplies the adsorption beds 23 of a MSOGS 24. The sample-gas leg 12 is similarly provided at its entrance with a filter 25 and a shroud 26. The shroud 26 receives a bleed of oxygen-enriched air from the product gas delivery line 27 of the MSOGS 24 by way of a duct 27a. The bridge pressure sensing ports 18, 19 are conduitly connected to the control ports 28, 29, respectively, of a suitably matched two-stage laminar flow proportional amplifier 30 driven by way of an adjustably restricted line 31 connecting first stage and second stage chambers of the amplifier 30 with the downstream portions of the two bridge sensor legs 11, 12 and the flueric aspirator 13. The ducts to the main jets 32, 33 of the amplifier 30 are arranged to receive an appropriate bleed of raw air from the supply line 22, taken by way of duct 22a and another freely venting shroud 34 and a filter 35. The amplified pressure signal ports 36, 37 of the amplifier 30 provide connection for the control signal output of the flueric partial pressure sensor 10.

As so far described, the flueric partial pressure sensor 10 corresponds in components and arrangement with that disclosed in U.S. Pat. No. 4,407,153. In accordance with the present invention, the output signals of the sensor are referenced to a datum pressure source, in this embodiment by the provision of a datum pressure chamber 38 that contains the three sets of filters and shrouds 20, 21; 25, 26; 35, 34; and which has restricted fluid communication with the interior of a crew cabin 39 by way of a restrictive flow orifice 40 and fluid communication with aircraft ambient atmospheric pressure by way of a pressure relief valve 41. The size of the orifice 40 is predetermined to allow the minimum outflow from the cabin 39 in achieving for the bridge sensor 10a the desired reference pressure intermediate that of cabin pressure and aircraft ambient atmospheric pressure at the maximum design ceiling, i.e. maximum operating altitude, of the aircraft. The pressure relief valve 41 is arranged to open at a predetermined aircraft altitude less than 30,000 feet (9,144 meters) and by holding a predetermined pressure difference across it, enables the desired datum pressure to be established in the chamber 38. The pressure signal ports 36, 37 of the amplifier 30 are connected to a pressure/electrical switch of a timer control unit 42 which is arranged for changing the cycle time of operation of the charge and vent valves 43 in sequencing the operation of the adsorption beds 23 of the MSOGS 24.

In operation of the flueric partial pressure sensor 10, air obtained from the MSOGS supply line 22 by way of duct 22b operates the flueric aspirator 13 and also by way of duct 22a fills the shrouds 21, 34. The air flow into these shrouds is sufficient to satisfy the requirements of the main jets 32, 33 of the two stages of the amplifier 30 and that of the reference leg 11 of the bridge sensor 10a, and to provide the minimum overflow or spillage from the shrouds that will prevent the ingress of contaminant ambient air. Sample-gas is similarly fed to the shroud 26, being obtained by way of duct 27a from MSOGS product gas delivery line 27 in amount to satisfy the requirements of the sample-gas leg 12 of the bridge sensor 10a and the minimum spillage from the shroud 26 that will prevent contamination of the sample-gas fed to the leg 12.

The aspirator 13 creates a sub-ambient pressure throughout the bridge sensor 10a and the amplifier 30 so that air, reference-gas and sample-gas are continuously drawn from the respective shrouds 34, 21, 26 to the aspirator 13 and ejected therefrom. The air passes to the main jets 32, 33 of the amplifier 30 and thence to the aspirator 13 by way of the restricted line 31 in the bridge sensor, while the reference-gas and the sample-gas pass through their respective bridge sensor legs 11, 12 to conjoin with the air from the main jets before entering the aspirator 13.

The values of the four resistors 14, 15, 16, 17 in the two legs 11, 12 of the bridge sensor 10a are selected to provide a small asymmetry between flow rates through the legs 11, 12 so that the bridge pressure sensing ports 18, 19 are in balance, (i.e. there is zero differential between the ports and the bridge provides a constant output signal) when the oxygen partial pressure value in the sample-gas is, say, 160 mmHg. The bridge pressure sensing ports will remain in balance irrespective of changes in absolute pressure, providing the oxygen partial pressure is maintained constant. It should be noted, however, that partial pressure is the product of gas concentration and ambient pressure, so that as altitude increases and ambient pressure falls the concentration of oxygen in ambient air remains substantially constant at about 20% whilst the partial pressure falls. Therefore, if the datum pressure in the datum pressure chamber 38 to which the reference-gas and sample-gas are pressure referenced changes the partial pressure of oxygen in the sample-gas will also change and the pressure sensing ports 18, 19 will be unbalanced until the oxygen concentration in the sample-gas is increased or decreased, as required, to restore the partial pressure of oxygen in the sample-gas to the value at which the bridge is balanced.

The pressure pertaining at pressure sensing ports 18, 19 is amplified in the two stages of the amplifier 30 and becomes effective at the respective control ports 28, 29 of the amplifier 30. However, the amplifier is slightly biased towards deflecting the first stage main jet towards one side when the bridge is balanced, so that one of the amplifier pressure signal ports 36/37 is signalled in the balanced condition of the bridge, and a pressure/electrical switch at the timer control unit 42 of the MSOGS 24 is held into one predetermined condition. If, for instance, the balanced condition of the bridge results in the control unit 42 giving the shorter of two time cycles to cause higher oxygen enrichment in the product gas, the arrangement is made such that a rise in oxygen partial pressure in the sample-gas above 160 mmHg results in the main jet 32 being switched from one side to the other so that the timer control unit is switched into a condition giving a longer time cycle to cause reduced oxygen enrichment of the product gas.

Let it be assumed that an aircraft having an oxygen enrichment system embodying the present invention has the crew cabin 39 pressurised to maintain a pressure equivalent of 8,000 feet (2,440 meters) at aircraft altitudes above this height and up to an altitude of, say, 45,000 feet (13,720 meters), and that the pressure relief valve 41 is arranged to commence opening at 25,000 feet (7,620 meters) aircraft altitude. The datum pressure to which the partial pressure sensor device 10 responds is the pressure in the datum pressure chamber 38 in which the shrouds 21, 26, 34, are situated. Consequently, until the pressure relief valve 41 opens the datum pressure is that pertaining in the cabin, being obtained through the restrictive flow orifice 40. However, when the valve 41 commences to open, the datum pressure decreases to a value intermediate that of the cabin and the aircraft ambient, but does not fall below a value insufficient to drive the partial pressure sensor.

The consequence of this change in the datum pressure is that the oxygen concentration in the sample-gas must change to maintain the bridge sensor in a state of balance. Thus under the control of the sensor, the MSOGS system will output a sample-gas the oxygen concentration of which will change from, nominally, 21% at sea level to 29% at 8,000 feet (2,440 meters) and remain at this value up to an aircraft altitude of 25,000 feet (7,620 meters). Thereafter as the aircraft continues to climb, because the pressure relief valve 41 opens and maintains a pressure difference between the interior of the datum pressure chamber 38 and aircraft ambient atmospheric pressure of, say, 5.8 psi (40 kPa), i.e. allows the pressure in the datum pressure chamber 38 to reduce progressively, the oxygen concentration in the sample-gas will increase progressively to approximately 50% at an aircraft altitude of 60,000 feet (18,290 meters) in order to hold the bridge sensor in balance.

Figure 2:
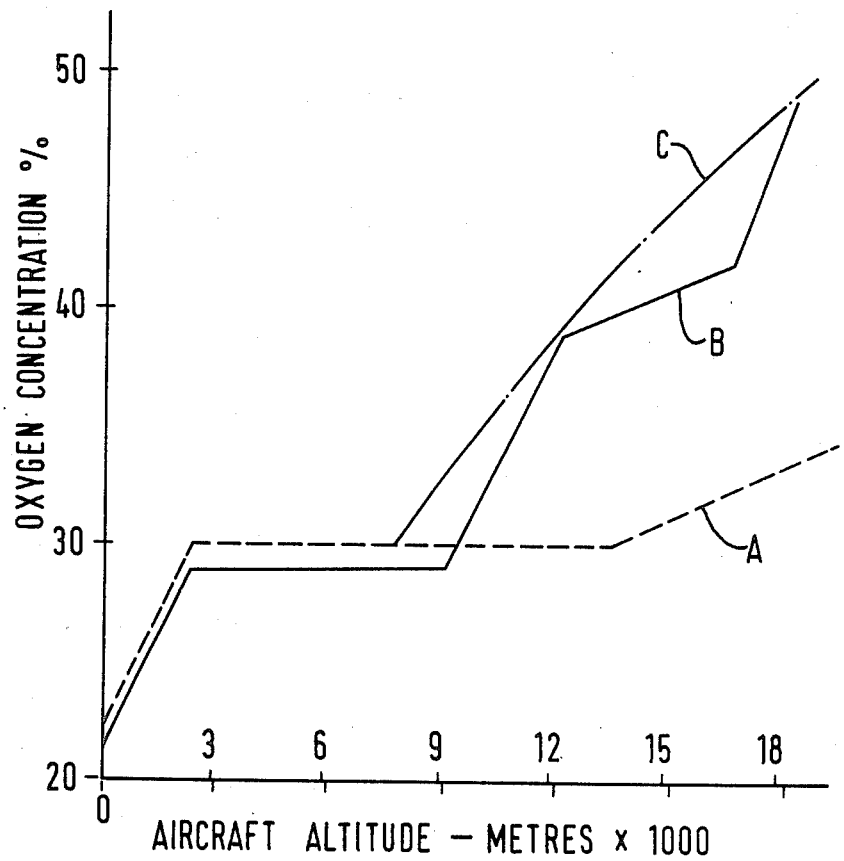
FIG. 2 is a graphical representation of various conditions of the partial pressure of oxygen related to the aircraft application of FIG. 1.

This is illustrated in FIG. 2 of which the vertical scale refers to the percentage value of the oxygen concentration in the oxygen-enriched air bled from the product delivery line 27 and sampled in the shroud 26, and the horizontal scale represents aircraft altitude. Curve A shows the oxygen concentration in oxygen enriched air supplied by the MSOGS necessary to maintain an oxygen partial pressure referenced to cabin pressure at a value which will cause the bridge pressure sensing ports to be balanced through an altitude range from sea level to 60,000 feet (18,290 meters). Curve B shows the medically desirable oxygen concentration in the enriched air breathed by the crew members in anticipation of possible instantaneous cabin depressurisation. Curve C shows the oxygen concentration in the oxygen enriched air appropriate to keeping the bridge sensing ports in balance through an altitude range from 25,000 feet (7,620 meters) to 60,000 feet (18,290 meters) when oxygen partial pressure is referenced to a datum pressure between cabin pressure and aircraft ambient atmospheric pressure, and which oxygen concentration accords closely to the medically desirable oxygen concentration for this altitude range shown in Curve B.

In a non-illustrated embodiment the partial pressure sensor 10 including the flueric aspirator 13 is contained entirely within the datum pressure chamber 38 which is comprised by a body shell having restricted fluid communication with the cabin 39 and being arranged for fluid communication with a region subject to ambient atmospheric pressure by way of the pressure relief valve 41. In this non-illustrated embodiment the restricted fluid communication with the cabin may comprise a check valve arranged to commence closing the fluid communication with the cabin as the pressure responsive valve commences to open so as to restrict and/or prevent outflow from the cabin to aircraft ambient atmosphere through the datum pressure chamber, the required differential between the pressure in the datum pressure chamber and ambient atmospheric pressure being substantially met by gas outflow from the partial pressure sensor shroud and flueric aspirator.

Whilst the disclosed embodiment relates to the control of a MSOGS by controlling the cycle time of the adsorption/desorption phases, the pressure signal output can be arranged to control the MSOGS by controlling a flow valve to regulate the vent flow from the beds or, alternatively, a spill valve in the product line.

The flueric partial pressure sensor can be preset or adjusted to have a particular set-point value other than 160 mmHg and to have one of a range of slopes, e.g. in FIG. 2 Curve A is representative of a set-point value of 170 mmHg.

The flueric partial pressure sensor may be utilised in an indicator or warning apparatus, e.g. the pressure signal output may be arranged to close an electrical contact when the balance of the sensor bridge departs to a certain value either side of the set-point value.

What is claimed is:

1. A method of changing control signals output by a flueric partial pressure sensor, said sensor comprising a flueric bridge having two legs adapted for respectively sensing a reference-gas and a sample-gas mixture, each leg including a linear flow resistor and an orifice flow resistor having values arranged to cause asymmetric flow rates through the two legs so that at a particular partial pressure of a constituent gas in the sample-gas mixture the bridge is in balance, the method including the steps of pressure referencing the reference-gas and the sample-gas mixture to a datum pressure and changing the datum pressure to change the control signals output by the sensor above a predetermined altitude.

2. A method of controlling an on-board oxygen enrichment of air system for an aircraft to automatically increase the oxygen concentration of oxygen-enriched air output by the system above a predetermined altitude, the system comprising a molecular sieve type gas separation system (MSOGS) arranged to deliver oxygen-enriched air to an outlet by adsorbing nitrogen from supply air fed to the MSOGS, and a flueric partial pressure sensor arranged to compare a reference bleed of supply air to the MSOGS with a sample bleed of oxygen-enriched air delivered by the MSOGS and to output signals for the control of the MSOGS, the method including the steps of referencing the reference bleed of supply air and the sample bleed of oxygen-enriched air to a datum pressure, and changing the datum pressure above a predetermined aircraft altitude to a pressure value intermediate the pressure within a cabin to which the oxygen-enriched air is supplied and the atmospheric pressure ambient to the aircraft whereby with change in aircraft altitude above the predetermined altitude the signals output by the sensor for control of the MSOGS are automatically varied to increase the oxygen concentration of the oxygen-enriched air.

3. A flueric partial pressure sensor including a flueric bridge having two legs, one of said legs sensing a reference-gas and the other of said legs sensing a sample-gas mixture, a linear flow resistor and an orifice flow resistor arranged in series in each of said legs, a pressure sensing port in each leg positioned between the linear flow resistor and the orifice flow resistor, a datum pressure chamber, a reference-gas supply line and a sample-gas mixture supply line to said bridge legs passing through said datum pressure chamber, means in said supply lines for pressure referencing the reference-gas and the sample-gas mixture to datum pressure in said datum pressure chamber, means in said datum pressure chamber providing a restricted flow communication with a first pressure region, pressure responsive means in said datum pressure chamber for providing communication with a second pressure region of different pressure from said first pressure region, the values of said linear flow resistors and orifice flow resistors being arranged to cause asymmetric flow rates through the two said legs so that the pressure sensing ports are in-balance at a predetermined partial pressure of a constituent gas in the sample-gas mixture whereby a change in datum pressure automatically changes control signals output by the sensor.

4. A flueric partial pressure sensor as claimed in claim 3, wherein the means in said supply lines for referencing the reference-gas and the sample-gas mixture to datum pressure comprise shrouds which are open to the datum pressure chamber.

5. An on-board oxygen enrichment of air system for an aircraft, including a molecular sieve type gas separation system (MSOGS) arranged to deliver oxygen-enriched air to an outlet by adsorbing nitrogen from supply air fed to the system and a flueric partial pressure sensor, said partial pressure sensor comprising a flueric bridge having two bridge legs, one of said bridge legs being arranged for sensing a reference bleed of supply air to the MSOGS and the other said bridge leg being arranged for sensing a sample bleed of oxygen-enriched air delivered by the MSOGS, a linear flow resistor and an orifice flow resistor arranged in series in each of said legs, a pressure sensing port in each leg positioned between the linear flow resistor and the orifice flow resistor, a datum pressure chamber, lines carrying the reference bleed of supply air and the sample bleed of oxygen-enriched air to said bridge legs passing through said datum pressure chamber, means in said supply lines for pressure referencing the reference bleed of supply air and the sample bleed of oxygen-enriched air to datum pressure in said datum pressure chamber, means in said datum pressure chamber providing a restricted flow communication with pressure in a cabin to which the oxygen-enriched air is supplied by the MSOGS, means in said datum pressure chamber for providing above a predetermined aircraft altitude a datum pressure value intermediate the pressure within the cabin and atmospheric pressure ambient to the aircraft, the values of said linear flow resistors and orifice flow resistors being arranged to cause asymmetric flow rates through the two said bridge legs so that the pressure sensing ports are in-balance at a predetermined partial pressure of oxygen in the sample bleed of oxygen-enriched air whereby with change in aircraft altitude above the predetermined altitude the signals output by the sensor for control of the MSOGS are automatically varied to increase the oxygen concentration of the oxygen-enriched air.

6. An on-board oxygen enrichment of air system as claimed in claim 5, wherein the means in said datum pressure chamber for providing a datum pressure value intermediate cabin pressure and aircraft ambient atmospheric pressure comprises a pressure responsive valve arranged to open the datum pressure chamber to aircraft ambient atmosphere.

7. An on-board oxygen enrichment of air system as claimed in claim 5, wherein the means in the supply lines for pressure referencing the reference bleed of supply air and the sample bleed of oxygen-enriched air to datum pressure comprise shrouds which are open to the datum pressure chamber.

8. An on-board oxygen enrichment of air system as claimed in claim 5, wherein the partial pressure sensor is wholly located within the datum pressure chamber.

* * * * *